(12) United States Patent
Chopra

(10) Patent No.: US 6,919,002 B2
(45) Date of Patent: Jul. 19, 2005

(54) NANOPORE SYSTEM USING NANOTUBES AND C60 MOLECULES

(75) Inventor: Nasreen G. Chopra, Belmont, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 412 days.

(21) Appl. No.: 10/150,672

(22) Filed: May 17, 2002

(65) Prior Publication Data
US 2003/0215376 A1 Nov. 20, 2003

(51) Int. Cl.⁷ .................. G01N 27/327; C23C 8/00; B01D 35/22
(52) U.S. Cl. .............. 204/403.06; 427/585; 210/348
(58) Field of Search .............. 204/403.01, 403.06, 204/403.07; 427/585–590; 210/348, 500.22

(56) References Cited

U.S. PATENT DOCUMENTS

2003/0116531 A1 * 6/2003 Kamins et al. .............. 216/41

OTHER PUBLICATIONS

Rijn et al. ("Nanosieves with microsystem technology for microfiltration applications," Nanotechnology 9 (1998) 343–345).*

Nathan R. Franklin and Hongjie Dai, "An Enhanced CFC Approach to Extensive Nanotube networks with Directionality", Advanced Materials, vol. 12, No. 12, pp. 890–894 (2000).

* cited by examiner

Primary Examiner—Alex Noguerola

(57) ABSTRACT

A nanopore system, and manufacturing method therefor, is provided with a substrate having a support material over the substrate. A nano-structure in the support material forms a nanopore.

38 Claims, 4 Drawing Sheets

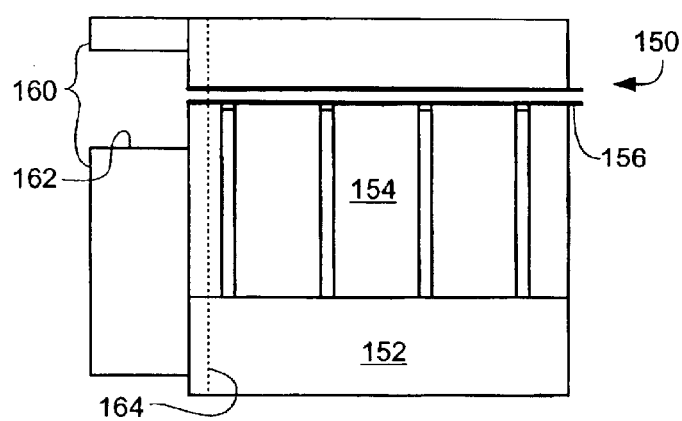
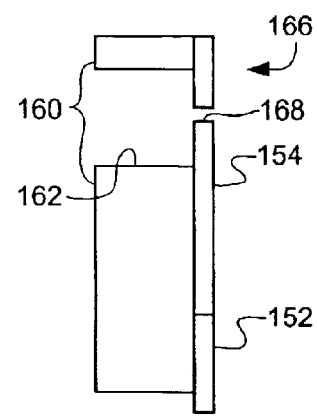
FIG. 8
FIG. 9
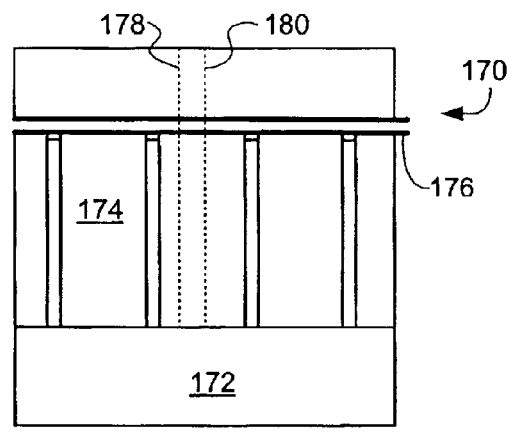
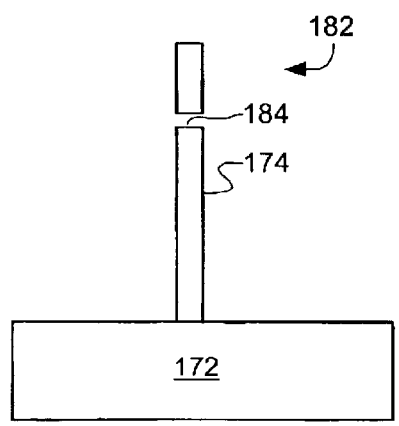
FIG. 10
FIG. 11

NANOPORE SYSTEM USING NANOTUBES AND C60 MOLECULES

BACKGROUND

1. Technical Field

The present invention relates generally to structures having sub-microscopic holes and more particularly to structures having nano-size pores.

2. Background Art

In many fields, especially biology and electronics, it has become important to be able to form smaller and smaller openings or pores in order to be able to advance the technology.

For example in biology, it has become important to be able to study single-stranded DNA and RNA in various fields, such as medicine and biological research. By studying DNA and RNA, various diseases can be detected and treated.

Unfortunately, the individual components of the DNA and RNA are nano-scale structures ($10^{-9}$ meter and below), which are sub-microscopic and cannot be read directly. For example, a single-stranded DNA is made up of a number of components called "nucleotides", which are designated by the letters A, C, G, and T (for adenine, cytosine, guanine, and thymine). The human genome is about 3.2 billion nucleotides long, which is analogous to a million-page book having different length words and 3,200 letters per page.

In order to be able to read a single-stranded DNA or RNA, it is necessary to be able to process one strand at a time. Unfortunately, there is currently no method that allows a direct measurement of one strand or even a method to line up the single strands in such a way that they may be read.

The ideal would be to electronically sense biological polymers, like RNA, DNA, and proteins, and also unlabeled polynucleotides at a molecular level so as to be able to characterize individual molecules with regard to length, type, and sequence. This would be accomplished by passing a strand of molecules through an opening or pore in a membrane and electronically sensing the molecules. In addition to a problem forming the electrodes for the electronic sensing, the major problem has been with making an opening or pore small enough that only one strand of molecules would pass through.

Methods used in the past for creating the required opening or pore included both organic and inorganic techniques. For example, a lipid bilayer membrane would be forced across a 30-$\mu$ hole in a piece of PTFE separating two compartments filled with buffer fluids. A chemical, ($\alpha$-hemolysin, would be added to one of the buffer-filled compartments and the $\alpha$-hemolysin would attack the lipid bilayer membrane for five minutes. Generally, a 2.6 nm diameter ion channel would form, after which the $\alpha$-hemolysin was immediately flushed out to prevent other pores from forming. However, there was no easy process of crosschecking that there was indeed only one pore and there was also an inability to place a single pore in a particular location.

Another approach used an organic pore synthesis using a freestanding silicon nitride film. The film is sputtered using a focused ion beam (FIB) with a feedback system that stops the FIB once ions are detected on the other side of the film. The process was then continued by redepositing silicon nitride in an effort to close up the opening to a desired size. This has also been problematic due to the difficulty of controlling the nitride deposition.

None of the prior art approaches were able to produce openings of a known size at a known location or assure only that a single pore was being manufactured. Further, the processes were not predictable and were time-consuming for forming single pores when successful.

A solution to this problem has been long sought, but has long eluded those skilled in the art.

SUMMARY OF THE INVENTION

The present invention provides a nanopore system, and manufacturing method therefor, with a substrate having a support structure over the substrate. A nano-structure in the support material forms a nanopore of a known size at a known location and assures only that a single pore being manufactured. In addition, the process can form the nanopore quickly.

Certain embodiments of the invention have other advantages in addition to or in place of those mentioned above. The advantages will become apparent to those skilled in the art from a reading of the following detailed description when taken with reference to the accompanying drawings.

BRIEF DESCRIPTION OF THE DRAWINGS

FIG. 8 is a view of an intermediate stage of manufacturing an alternate embodiment in accordance with the present invention;

FIG. 9 is the structure of FIG. 8 in the alternate embodiment in accordance with the present invention;

FIG. 10 is a view of an intermediate stage of manufacturing a further alternate embodiment in accordance with the present invention;

FIG. 11 is the structure of FIG. 10 in the further alternate embodiment in accordance with the present invention;

DETAILED DESCRIPTION OF THE INVENTION

Figure 1:
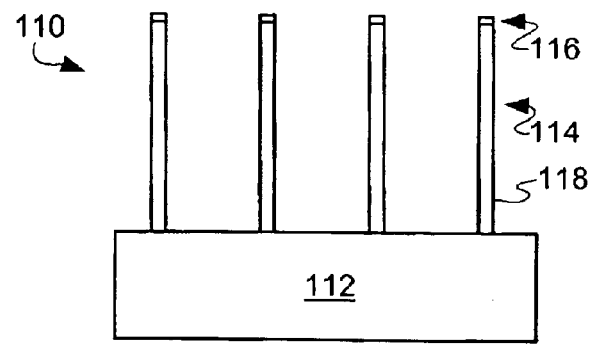
FIG. 1 is a view of a nanopore system support in accordance with the present invention.

Referring now to FIG. 1, therein is shown a nanopore system support 110 in accordance with the present invention. The nanopore system support 110 includes a substrate 112 having pillars 114 topped by a catalyst precursor 116.

The term "horizontal" as used herein is defined as a plane parallel to the conventional plane or surface of the substrate 112 regardless of its orientation. The term "vertical" refers to a direction perpendicular to the horizontal as just defined. Terms, such as "on", "above", "below", "side", "higher", "lower", "over", and "under", are defined with respect to the horizontal plane.

The substrate 112 can be a silicon substrate, such as a silicon wafer, and the plurality of pillars 114 can be formed by etching a silicon wafer vertically to form the pillars to a desired height. For example, the plurality of pillars 114 are approximately 10µ high and spaced apart as will be subsequently described.

The catalyst precursor 116 can be of a plurality of materials, such as iron, cobalt, nickel, and a combination thereof. The catalyst precursor 116 is at the very top of the plurality of pillars 114 and is generally deposited by a stamping technique.

As an option for certain purposes, a conductive material 118, such as copper or aluminum, can also be deposited on the sides of the plurality of pillars 114 or the pillars can be made of such conductive materials.

Figure 2:
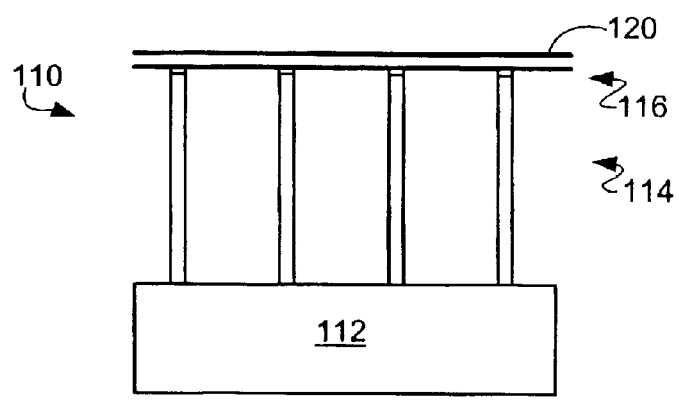
FIG. 2 is the structure of FIG. 1 with a nanotube grown thereon.

Referring now to FIG. 2, therein is shown the structure of FIG. 1 having a nano-structure or nanotube 120 grown thereon. The nanotube 120 forms on the catalyst precursor 116 on the plurality of pillars 114. The catalyst precursor 116 is conditioned to favor enhanced directional growth so that the nanotube 120 and other nanotubes grow in a preferential direction. As a result, the nanotube 120 extends across two or more of the plurality of pillars 114.

The nanotube 120 can be described as a long thin strip cut out of a single atomic layer of a material such as carbon and rolled lengthwise to form a cylinder with a nanometer scale diameter and a length on the order of microns. For example, the nanotube 120 can have a wall thickness of one atom thickness and an inside wall-to-wall diameter of 1 to 5 nanometers (nm). Also, by way of example, nanotube structures can be made of a multi-wall nanotube to have inner diameters up to 20 nanometers.

There are several well known techniques for manufacturing single-walled nanotubes (SWNT) of carbon. Laser ablation techniques have produced tubes with uniform diameters of 1.3 nm and chemical vapor deposition techniques have produced very high quality nanotubes that vary in diameter from 1.2 nm.

The chemical vapor deposition process for growing the nanotube 120 starts by placing the substrate 112 into a furnace at approximately 700° C. to 1000° C. while flowing a carbon containing gas, such as methane, across the catalyst precursor 116 until the nanotube 120 forms.

Figure 3:
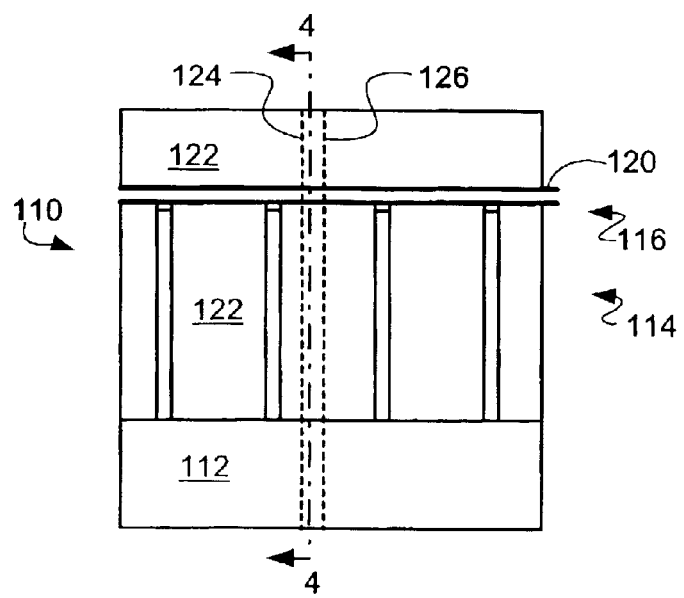
FIG. 3 is the structure of FIG. 2 with the nanotube embedded in a support material.

Referring now to FIG. 3, therein is shown the nanotube 120 embedded in a support material or matrix material 122. The matrix material 122 can be a material such as silicon dioxide, silicon nitride, an insulating resin, or even an epoxy. The precise location of the nanotube 120 is fixed by the height of the plurality of pillars 114 above the substrate 112 and the nanotube 120 will be radially surrounded and supported by the matrix material 122.

If electrical contact to the nanotube 120 is not required through the plurality of pillars 114, the nanotube 120 could be formed without the plurality of pillars 114 by forming a first portion of the matrix material 122 to the desired height, forming the nanotube 120, and forming a second portion of the matrix material 122 to completely embed the nanotube 120.

The matrix material 122 is capable of being sliced at any location, such as along slice lines 124 and 126. There are a number of ways that the slices can be made along the slice lines 124 and 126 including diamond sawing and microtoming. Alternatively the device may be ground on a grinding wheel for example from the edge perpendicular to the tube to result in a piece of desired thickness.

It will be noted that the slice lines 124 and 126 can be spaced at any distance including through the plurality of pillars 114. In situations where conductive contact is desired to the nanotube 120, the distance between the slice lines 124 and 126 can be varied to span one or more of the plurality of pillars 114 covered by the conductive material 118.

Figure 4:
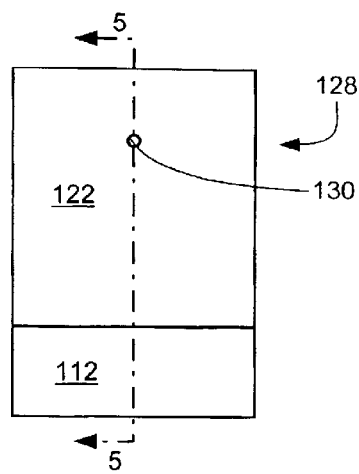
FIG. 4 is the structure of FIG. 3 showing a nanopore system.

Referring now to FIG. 4, therein is shown the structure of FIG. 3 along line 4—4 of FIG. 3. A nanopore system 128 has been formed from the material between the slice lines 124 and 126 of FIG. 3. While the nanopore system 128 could include the sliced-up portion of the nanotube 120, the nanopore system 128 may be placed in oxygen and heated to about 400° C. to oxidize the carbon into carbon dioxide and remove it entirely from the nanometer opening, to form a nanopore 130.

Figure 5:
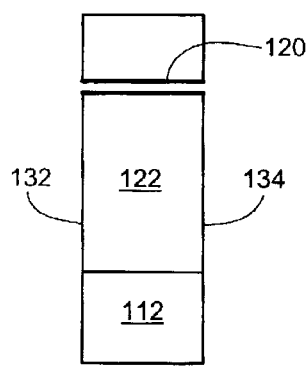
FIG. 5 is the structure of FIG. 4 with a view of the nanotube and side surfaces.

Referring now to FIG. 5, therein is shown the structure of FIG. 4 along line 5—5. In FIG. 5, the nanotube 120 is shown along with parallel side surfaces 132 and 134.

Figure 6:
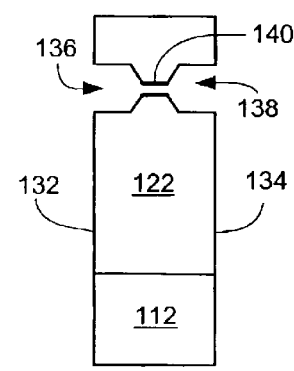
FIG. 6 is the structure of FIG. 5 after shortening the nanotube.

Referring now to FIG. 6, therein is shown the structure of FIG. 5 after shortening of the nanotube 120. In some applications, a nanotube segment 140 of the nanotube 120 may be desired rather than the full length between slices in forming the nanopore system 128. In such a situation, any one of numerous techniques, such as etching, can be used to provide reliefs in the parallel side surfaces 132 and/or 134. It will be understood that in many situations one relief 136 will be sufficient but in others a second relief 138 may be desired to form the nanotube segment 140. In the extreme, the first and second reliefs 136 and 138 can meet to eliminate the nanotube segment 140 and leave just a nanopore.

Figure 7:
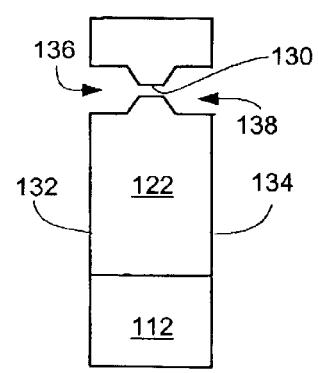
FIG. 7 is the structure of FIG. 6 after removal of the short nanotube.

Referring now to FIG. 7, therein is shown the structure of FIG. 6 after removal of the segment 140 of FIG. 6 to form a nanopore 142. It will be understood that with or without the nanotube segment 140, a pore made using a nanotube, or a multi-wall nanotube, is still defined as a "nanopore" for purposes of the present invention.

Referring now to FIG. 8, therein is shown a view of an intermediate stage of manufacturing an alternate embodiment in accordance with the present invention. A nanopore system chip 150 has a substrate 152 with a matrix material 154 having an embedded nanotube 156. At one side of the nanopore system chip 150, a support frame 160 has been attached. The support frame 160 has an opening 162 connected to the embedded nanotube 156. A slice line 164 is shown.

Referring now to FIG. 9, therein is shown a nanopore system 166, the alternate embodiment in accordance with the present invention. Essentially, a slice is made along the slice line 164 of FIG. 8 to produce the nanopore system 166 where the support frame 160 supports a thin slice of the nanopore system chip 150, which contains a nanopore 168.

Referring now to FIG. 10, therein is shown an intermediate stage of manufacturing a further alternate embodiment in accordance with the present invention. A nanopore system chip 170 has a substrate 172 with a matrix material 174 having an embedded nanotube 176. Two slice lines 178 and 180 are shown.

Referring now to FIG. 11, therein is shown a nanopore system 182, the further alternate embodiment in accordance with the present invention. The nanopore system 182 has the substrate 172 with a portion between the slice line 178 and the slice line 180 having a nanopore 184.

Figure 12:
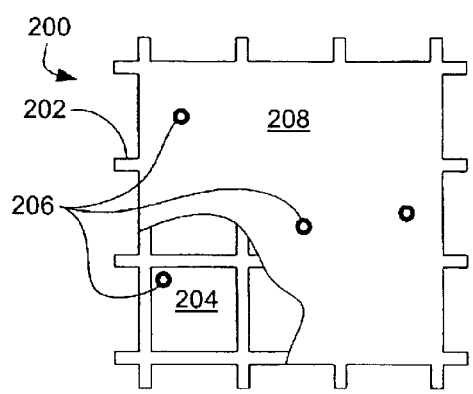
FIG. 12 is a view of an intermediate stage of manufacturing a still further alternate embodiment in accordance with the present invention.

Referring now to FIG. 12, therein is shown a nanopore support system 200 in accordance with the present invention.

The nanopore support system 200 includes a support grid 202, which may be the support grid of a transmission electron microscope (TEM) with a substrate 204. Dispersed on the substrate 204 is a plurality of nano-structures or $C_{60}$ molecules 206.

The $C_{60}$ molecules 206 have icosahedral structures and are commonly known as Buckminsterfullerene molecules. Essentially, they are spherical soccer-ball structures with 0.7 nm diameters, which are formed by placing a carbon atom at each of 60 vertices of a molecule.

The monodispersion of the $C_{60}$ molecules is accomplished by dissolving a small number of $C_{60}$ molecules in toluene and dispensing the resulting solution onto the substrate 204 and evaporating the toluene solvent. A support material or matrix material 208, such as silicon dioxide, silicon nitride, an insulating resin, or an epoxy , would be deposited over the $C_{60}$ molecules 206 and the substrate 204.

Subsequently, one of the $C_{60}$ molecules 206 will be identified in a desirable location. A photoresist (not shown) will be deposited as a mask over the matrix material 208 and processed to expose the matrix material 208 in the region of the one $C_{60}$ molecule. The exposed matrix material 208 will be removed and the one $C_{60}$ molecule will be removed. The substrate 204 will be removed so as to leave one $C_{60}$ molecule embedded in the matrix material 208 supported by the support grid 202.

Figure 13:
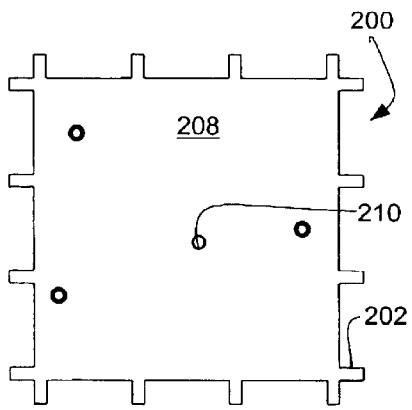
FIG. 13 is the structure of FIG. 12 in the still further alternate embodiment in accordance with the present invention.

Referring now to FIG. 13, therein is shown the structure of FIG. 12 after processing to form a nanopore 210 in the matrix material 208. The nanopore 210 is formed by removing the matrix material 208 from above the $C_{60}$ molecule 206 of FIG. 12 by a process such as ion milling and heating the structure to 400° C. in a controlled oxygen atmosphere where the carbon atoms will decompose into carbon monoxide and carbon dioxide.

While this technique has the inability to place the nanopore 210 in an exact position due to the random distribution of the molecules on the surface, it provides an extremely precise nanopore 210 because the pore size is determined by the extremely well-defined diameter of the $C_{60}$ molecule.

The present invention has the advantages that the pore can have a very precise diameter, that a single nanopore can be opened, and that the nanopore can generally be in a known location. An additional advantage is that the present invention provides an extremely predictable manufacturing process for nanopores.

Figure 14:
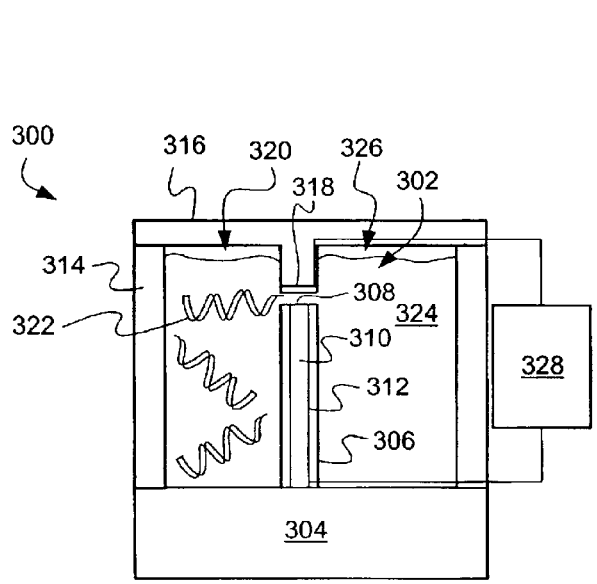
FIG. 14 is a cross-sectional view of a biological polymer sensor according to the present invention.

Referring now to FIG. 14, therein is shown a cross-sectional view of a biological polymer sensor 300 in accordance with the present invention. A nanopore system 302 has the substrate 304 with a sliced portion 306 having a nanopore 308. The sliced portion 306 contains a pillar 310 coated with a conductor 312, which is conductively connected to the bottom portion of the nanopore 308. The sliced portion 306 has been reduced in height to expose the top portion of the nanopore 308 and is surrounded by sidewalls 314. A cap 316 containing an electrode 318 forms the top portion of the nanopore 308. The sliced portion 306 and the cap 316 divide the enclosing sidewalls 14 into two compartments. A first compartment 320 contains strands of biological polymers 322 in a supporting fluid 324. Various means, such as fluid pressure or electrical potential, can be used to cause translocation of the biological polymers 320 through the nanopore 308 into the second compartment 326. A detector 328 is connected to the conductor 312 and electrode 318 to read molecules in the stands of biological polymers 322 as they pass through in the nanopore 308.

Figure 15:
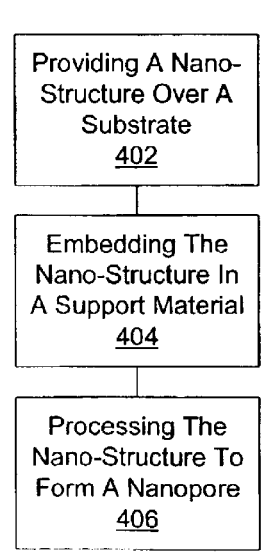
FIG. 15 is a flow chart of the method of the present invention.

Referring now to FIG. 15, therein is shown a simplified flow chart 400 according to the present invention having a process 402 of providing a nano-structure over a substrate, a process 404 of embedding the nano-structure in a support material, and a process 406 of processing the nano-structure to form a nanopore.

The biological polymer sensor 300 can electronically sense translocating molecules so as to be able to characterize individual molecules with regard to length, type, and sequence in the case of biological polymers like RNA, DNA, and proteins, and also unlabeled polynucleotides.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations which fall within the spirit and scope of the included claims. All matters set forth herein or shown in the accompanying drawings are to be interpreted in an illustrative and non-limiting sense.

The invention claimed is:

1. A method for manufacturing a nanopore system comprising:

providing a nano-structure over a substrate;

embedding the nano-structure in a support material; and processing the nano-structure to form a nanopore.

2. The method as claimed in claim 1 wherein processing the nano-structure includes removing the nano-structure from the support material.

3. The method as claimed in claim 1 wherein providing the nano-structure includes:

forming pillars on the substrate;

placing a catalyst precursor on the pillars; and depositing a nanotube on the pillars.

4. The method as claimed in claim 1 wherein:

providing the nano-structure includes providing a spherical molecule; and processing the nano-structure includes removing the support material above the spherical molecule.

5. The method as claimed in claim 1 including:

processing the substrate and the support material to form parallel surfaces with a surface intersecting the nano-structure.

6. The method as claimed in claim 1 including:

processing the substrate and the support material to form parallel surfaces with the support material having a relief provided therein intersecting the nano-structure.

7. The method as claimed in claim 1 including:

processing the substrate to a first size; and processing the support material to a second size smaller than the first size.

8. The method as claimed in claim 1 including:

bonding a support frame on the support material.

9. The method as claimed in claim 1 including:

forming means around the support material for translocating molecules through the nanopore.

10. The method as claimed in claim 1 including:

forming a further material around the support material for translocating molecules through the nanopore; and providing an electronic detection system for electronically sensing translocating molecules in the nanopore.

11. A method for manufacturing a nanopore system comprising:
providing a carbon nano-structure over a silicon substrate;
embedding the carbon nano-structure in a matrix material; and
processing the carbon nano-structure to form a nanopore.

12. The method as claimed in claim 11 wherein processing the carbon nano-structure includes removing the carbon nano-structure from the matrix material by exposing to oxygen.

13. The method as claimed in claim 11 wherein providing the carbon nano-structure includes:
forming pillars on the silicon substrate;
placing a catalyst precursor on the pillars, the catalyst precursor conditioned to favor enhanced directional growth; and
growing a carbon nanotube on the pillars.

14. The method as claimed in claim 11 wherein:
providing the carbon nano-structure includes:
providing a $C_{60}$ molecule,
dispensing the $C_{60}$ molecule in a solvent onto the silicon substrate, and
evaporating the solvent; and
processing the carbon nano-structure includes:
removing the matrix material above the $C_{60}$ molecule,
removing the substrate below the C60 molecule, and
exposing the $C_{60}$ molecule to oxygen.

15. The method as claimed in claim 11 including:
processing the silicon substrate and the matrix material to form parallel surfaces with a surface intersecting the carbon nano-structure.

16. The method as claimed in claim 11 including:
processing the silicon substrate and the matrix material to form parallel surfaces with the matrix material having a relief provided therein intersecting the carbon nano-structure.

17. The method as claimed in claim 11 including:
processing the silicon substrate to a first size; and
processing the matrix material to a second size smaller than the first size.

18. The method as claimed in claim 11 including:
bonding a support frame on a first surface of the matrix material, the matrix material having an opening provided therein adjacent the carbon nano-structure; and
processing the matrix material to form a second surface proximate the first surface.

19. The method as claimed in claim 11 including:
forming means around the matrix material for translocating biological polymer molecules through the nanopore.

20. The method as claimed in claim 11 including:
forming a further material around the matrix material for containing biological polymer molecules;
providing a mechanism for translocating biological polymer molecules through the nanopore; and
providing an electronic detection system for electronically reading translocating biological polymer molecules in the nanopore.

21. A nanopore system comprising:
a substrate;
a support material over the substrate; and
a nano-structure in the support material formed into a nanopore.

22. The nanopore system as claimed in claim 21 wherein the nano-structure includes:
pillars on the substrate;
a catalyst precursor on the pillars; and
a nanotube on the pillars.

23. The nanopore system as claimed in claim 21 wherein:
the nano-structure is a spherical molecule; and
the support material is absent above the spherical molecule.

24. The nanopore system as claimed in claim 21 wherein:
the substrate and the support material have parallel surfaces with a surface intersecting the nano-structure.

25. The nanopore system as claimed in claim 21 wherein:
the substrate and the support material have parallel surfaces with the support material having a relief provided therein intersecting the nano-structure.

26. The nanopore system as claimed in claim 21 wherein:
the substrate is a first size; and
the support material is a second size smaller than the first size.

27. The nanopore system as claimed in claim 21 including:
a support frame on the support material.

28. The nanopore system as claimed in claim 21 including:
a further material around the support material for translocating molecules through the nanopore.

29. The nanopore system as claimed in claim 21 including:
a further material around the support material for translocating molecules through the nanopore; and an electronic detection system for electronically sensing translocating molecules in the nanopore.

30. A nanopore system comprising:
a silicon substrate;
a matrix material over the silicon substrate; and
a carbon nano-structure formed into a nanopore.

31. The nanopore system as claimed in claim 30 wherein providing the carbon nano-structure includes:
pillars on the silicon substrate;
a catalyst precursor on the pillars, the catalyst precursor conditioned to favor enhanced directional growth; and
a carbon nanotube on the plurality of pillars.

32. The nanopore system as claimed in claim 30 wherein:
the matrix material has a $C_{60}$ molecule-sized nanopore provided there through.

33. The nanopore system as claimed in claim 30 wherein:
the carbon nano-structure is a carbon nanotube; and
the silicon substrate and the matrix material have parallel surfaces with the parallel surfaces intersecting the carbon nanotube.

34. The nanopore system as claimed in claim 30 wherein:
the carbon nano-structure is a carbon nanotube; and
the silicon substrate and the matrix material form parallel surfaces with the matrix material having a relief provided therein intersecting the carbon nanotube.

35. The nanopore system as claimed in claim 30 wherein:
the silicon substrate is of a first size; and
the matrix material is of a second size smaller than the first size, the matrix material having a nanotube extending therethrough.

36. The nanopore system as claimed in claim 30 including:
   a support frame bonded on a first surface of the matrix material, the matrix material having an opening provided therein adjacent the carbon nano-structure; and
   the matrix material having a second surface proximate the first surface intersecting the carbon nanostructure.

37. The nanopore system as claimed in claim 30 including:
   means around the matrix material for translocating biological polymer molecules through the nanopore.

38. The nanopore system as claimed in claim 30 including:
   a further material around the matrix material for containing biological polymer molecules;
   a mechanism for translocating biological polymer molecules through the nanopore; and
   an electronic detection system for electronically reading translocating biological polymer molecules in the nanopore.

* * * * *